United States Patent [19]

Carney et al.

[11] 4,208,407
[45] Jun. 17, 1980

[54] 5-DEOXYFORTIMICIN A, 2,5-DIDEOXYFORTIMICIN A AND THE CORRESPONDING 4-N-ACYL AND ALKYL FORTIMICIN B DERIVATIVES THEREOF AND INTERMEDIATES THEREFOR

[75] Inventors: Ronald E. Carney, Gurnee; Jerry R. Martin, Waukegan; James B. McAlpine, Libertyville; John S. Tadanier, Waukegan, all of Ill.

[73] Assignee: Abbott Laboratories, North Chicago, Ill.

[21] Appl. No.: 9,638

[22] Filed: Feb. 5, 1979

[51] Int. Cl.² .................. A61K 31/71; C07H 15/22
[52] U.S. Cl. ............................. 424/180; 536/17 R
[58] Field of Search ...................... 536/17; 424/180

[56] References Cited

U.S. PATENT DOCUMENTS

| | | | |
|---|---|---|---|
| 3,931,400 | 1/1976 | Nara et al. | 424/118 |
| 3,976,768 | 8/1976 | Nara et al. | 424/118 |
| 4,091,032 | 5/1978 | Tadanier et al. | 536/17 |

*Primary Examiner*—Johnnie R. Brown
*Attorney, Agent, or Firm*—Robert L. Niblack; Gildo E. Fato; Joyce R. Niblack

[57] ABSTRACT

5-Deoxyfortimicin A, 2,5-dideoxyfortimicin A and the corresponding 4-N-acyl and alkyl fortimicin B derivatives thereof, pharmaceutically acceptable salts thereof, intermediates therefor, and pharmaceutical compositions containing the compounds of this invention. The fortimicin derivatives are represented by the formula:

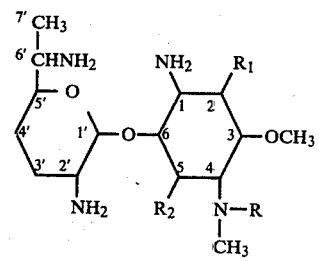

wherein R is selected from the group consisting of acyl, hydroxyacyl, aminoacyl, N-monoloweralkylaminoacyl, N,N-diloweralkylaminoacyl, hydroxyacyl, hydroxy-substituted aminoacyl or an amino acid residue other than glycyl, loweralkyl, aminoloweralkyl, hydroxyloweralkyl, N-monoloweralkylaminoloweralkyl, N-N-diloweralkylaminoloweralkyl or hydroxy-substituted aminoloweralkyl; $R_1$ is hydrogen or hydroxy; and $R_2$ is hydrogen or hydroxy with the limitation that either $R_1$ and $R_2$ each are hydrogen or when only one of $R_1$ or $R_2$ are hydrogen, $R_2$ is hydrogen and $R_1$ is hydroxy and $R_1$ and $R_2$ both cannot be hydroxy.

20 Claims, No Drawings

5-DEOXYFORTIMICIN A, 2,5-DIDEOXYFORTIMICIN A AND THE CORRESPONDING 4-N-ACYL AND ALKYL FORTIMICIN B DERIVATIVES THEREOF AND INTERMEDIATES THEREFOR

BACKGROUND OF THE INVENTION

It is known that the anti-bacterial spectrum and pharmacological properties of many naturally produced aminoglycoside antibiotics can be altered by structural modifications. For example, certain chemical modifications in the gentamicin and kanamycin family of aminoglycoside antibiotics provide structures which are less toxic than the parent antibiotic. Further, certain chemical modifications in the above family series alter the antibiotic spectrum advantageously either by increasing the intrinsic activity or increasing their activity against resistant strains.

Recently, a new family of aminoglycoside antiobiotics, the fortimicins, has been identified. See U.S. Pat. Nos. 3,976,768 and 3,931,400 which disclose the naturally produced parent antibiotics, Fortimicin A and Fortimicin B.

Historically, once an aminoglycoside antibiotic has been in clinical use for awhile, resistant microorganisms arise. In many cases, the resistance is R-Factor mediated and is attributed to the ability of the bacteria to enzymatically modify the amino or hydroxyl groups of the aminglycoside antibiotic. It is known that in the naturally occurring fortimicin aminoglycoside antiobiotics, blocking the hydroxyl group inactivates the antiobiotics.

The present invention provides 5-deoxyfortimicins and 2,5-dideoxyfortimicins which could not be inactivated by R-factor carrying microorganisms which could modify the hydroxyl groups of the parent fortimicins.

SUMMARY

5-Deoxyfortimicin A, 2,5-dideoxyfortimicin A, and the corresponding 4-N-alkyl and 4-N-acyl fortimicin B derivatives are provided by the present invention as well as their pharmaceutically acceptable salts, intermediates useful in the preparation of the antibiotics of this invention, processes for making the compounds, and compositions employing the novel antibiotics as the active component of the composition.

The antibiotics are administered by parenteral routes of administration in daily dosages of from about 10 to about 200 mg/kg of body weight daily to patients infected by susceptible gram negative or gram positive bacteria such as *Escherichia coli, Streptococcus faecalis, Pseudomonas aeruginosa, Bacillus subtilis, Proteus vulgaris, Shigella sonnei, Salmonella typhi* and *Klebsiella pneumoniae*.

DETAILED DESCRIPTION OF THE INVENTION

This invention provides new fortimicin antibiotics, 5-deoxyfortimicin A, 2,5-dideoxyfortimicin A and the corresponding 4-N-alkyl and 4-N-acyl fortimicin B derivatives represented by formulae I and II respectively.

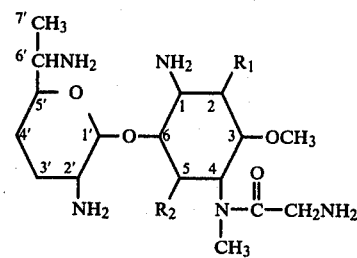

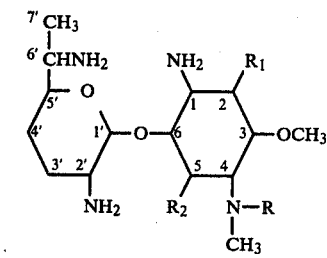

wherein R is selected from the group consisting of acyl, hydroxyacyl, aminoacyl, N-monoloweralkylaminoacyl, N,N-diloweralkyl, aminoacyl, hydroxyacyl, hydroxy-substituted aminoacyl or an amino acid residue other than glycyl, loweralkyl, aminoloweralkyl, hydroxyloweralkyl, N-monoloweralkylaminoloweralkyl, N-N-diloweralkylaminoloweralkyl or hydroxy-subsituted aminoloweralkyl; $R_1$ is hydrogen or hydroxy; and $R_2$ is hydrogen or hydroxy with the limitation that either $R_1$ and $R_2$ each are hydrogen or when only one of $R_1$ or $R_2$ are hydrogen, $R_2$ is hydrogen and $R_1$ is hydroxy and $R_1$ and $R_2$ both cannot be hydroxy.

The 2,5-dideoxyfortimicins of this invention are represented by Formulae III and IV as follows wherein R is as defined in Formulae I and II:

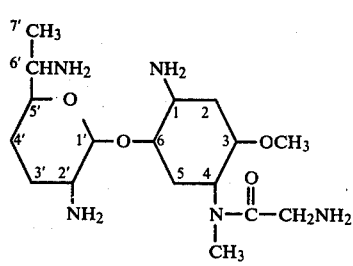

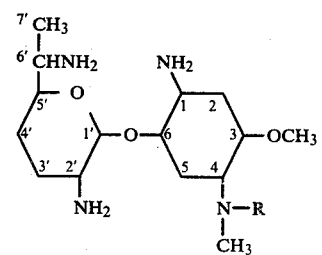

The 5-deoxyfortimicins of this invention are repesented by Formulae V and VI as follows wherein R is as defined in Formulae I and II:

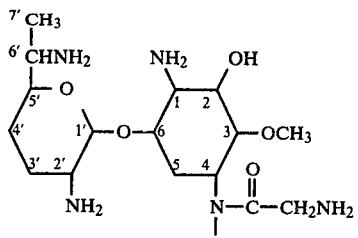  (V)

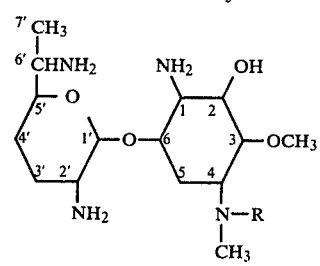  (VI)

The term "acyl", as used herein, refers to acyl groups represented by the formula $$-\overset{O}{\underset{\parallel}{C}}-R_1$$

wherein $R_1$ is loweralkyl, i.e., acetyl, propionyl, butyryl, and the like. The term "amino acid residue" refers to a D, L or DL amino acid residue such as glycyl, alanyl, sarcosyl, leucyl, isoleucyl, valyl, phenylalanyl, tyrosyl, tryptophyl, seryl, threonyl, methionyl, glutamyl, glutaminyl, aspartyl, asparaginyl, prolyl, histidyl, lysyl, arginyl and the like.

The term "loweralkyl" refers to straight or branched chain alkyl groups having from 1 to 6 carbon atoms, i.e., methyl, ethyl, n-propyl, iso-propyl, n-butyl, sec-butyl, tert-butyl, n-pentyl, n-hexyl, and the like.

The substituted alkyl groups are well known in the art and include, for example, aminomethyl, β-aminoethyl, N-methylaminoethyl, N,N-dimethylaminopropyl, etc.

The term "pharmaceutically acceptable salts" are the non-toxic acid addition salts prepared by reacting the base with a suitable organic or inorganic acid. Representative salts include the hydrochloride, hydrobromide, sulfate, bisulfate, acetate, oxalate, valerate, oleate, palmitate, stearate, laurate borate, benzoate, lactate, phosphate, tosylate, citrate, maleate, fumarate, succinate, tartrate, napsylate and the like.

In addition to the above-described antibiotics of Formulae I and II and their salts, this invention also provides intermediates which are useful in preparing the compounds of Formulae I and II.

Intermediates of Formulae VII and VIII are useful in preparing the compounds of Formulae III and IV. Intermediates of Formulae IX and X are useful in preparing the compounds of Formulae V and VI.

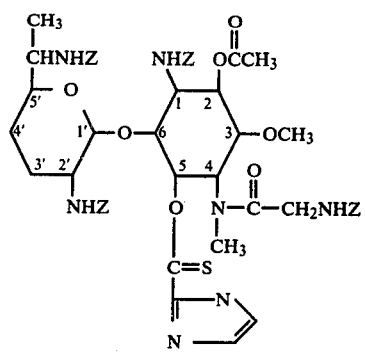  (VII)

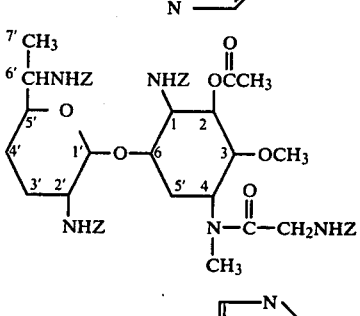  (VIII)

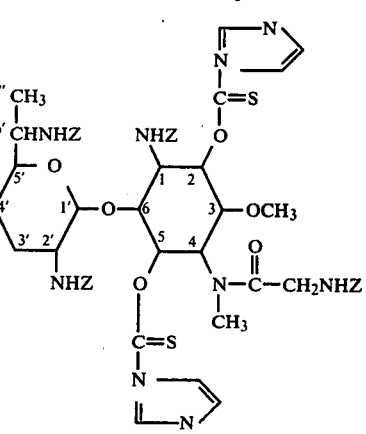  (IX)

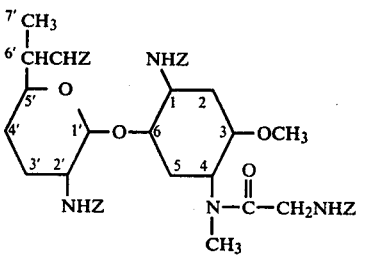  (X)

In the above formulae, Z stands for benzyloxycarbonyl.

EXAMPLE 1

Tetra-N-benzyloxycarbonylfortimicin A-2,5-di-O-thiocarbonylimidazole

Tetra-N-benzyloxycarbonylfortimicin A(10 g, 10.62 millimole) is dissolved in ethyl acetate (400 ml) N,N-thiocarbonyldiimidazole (4.8 g, 27 millimole) is added and the mixture is heated under reflux overnight. Solvent is then removed and the residue is chromatographed on a column of silica gel to give tetra-N-benzyloxycarbonylfortimicin A-2,5-di-0-thiocarbonylimidazolide (9.0 g).

EXAMPLE 2

2,5-Dideoxytetra-N-benzyloxycarbonylfortimicin A

A solution of tetra-N-benzyloxycarbonylfortimicin A-2,5-di-0-thiocarbonylimidazole (9.0 g 7.75 millimole) in dioxane (250 ml) is added dropwise to a solution of tri-n-butylstannane (12.5 ml) in dioxane (500 ml). The mixture is heated under reflux in an atmosphere of nitrogen for 6 hours. Solvent is removed and the residue is chromatographed on a column of silica gel to give 2,5-dideoxytetra-N-benzyloxycarbonylfortimicin A (3.8 g).

EXAMPLE 3

2,5-Dideoxyfortimicin A tetrahydrochloride 2,5-Dideoxytetra-N-benyloxycarbonylfortimicin A (160 mg, 0.176 millimole) is dissolved ih methanolic hydrogen chloride (25 ml, 0.2 N) and shaken in an atmosphere of hydrogen with 5% palladium on carbon (160 mg) for four hours. The catalyst was removed by filtration and the filtrate evaporated to dryness to yield 2,5-dideoyfortimicin A tetrahydrochloride (67 mg).

EXAMPLE 4

2-O-Acetyltetra-N-benzyloxycarbonylfortimicin A-5-O-thiocarbonylimidazolide

To a solution of 2-O-acetyltetra-N-benzyloxycarbonylfortimicin A(2.5 g, 2.54 millimole) in dichloroethane (100 ml) are added N,N'-thiocarbonyldiimidazole (2.0 g, 11.2 millimole) and triethylamine (1.0 ml). The mixture is heated at reflux and after five hours, solvent is removed. Chromatography of the residue over a column of silica gel gives 2.53 g of 2-O-acetyltetra-N-benzyloxycarbonylfortimicin A-5-O-thiocarbonylimidazolide.

Anal. Calcd for $C_{55}H_{63}N_7O_{15}S$: C,60.37; H, 5.80; N,8.96; S, 2.93.

Found : C,60.19; H, 5.67; N,8.86; S,2.74.

Example 5

2-O-Acetyl-5-deoxytetra-N-benzyloxycarbonylfortimicin A

A solution of 2-O-acetyltetra-N-benzyloxycarbonyl-fortimicin A-5-O-thiocarbonylimidazolide (2.1g 1.93 millimole) in dioxane (60 ml) is added dropwise to a solution of tri-n-butylstannane (4.0 ml) in dioxane (150 ml). The mixture is heated under reflux in an atmosphere of nitrogen for six hours. Solvent is removed and the residue is chromatographed on a column of silica gel to give 2-O-acetyl-5-deoxytetra-N-benzyloxycarbonyl-fortimicin A (1.33 g).

EXAMPLE 6

5-Deoxytetra-N-benzyloxycarbonylfortimicin A

A solution of 2-O-acetyl-5-deoxytetra-N-benzyloxycarbonylfortimicin A (1.25 g, 1.20 millimole) in methanol (25 ml) is treated with sodium ethoxide (106 mg, 1.55 millimole) at room temperature. After being stirred for one hour, the reaction mixture is poured into seven volumes of water and the product extracted into ethyl acetate. The ethyl acetate solution is dried over magnesium sulfate, filtered and the filtrate is evaporated to give 5-deoxytetra-N-benzyloxycarbonylfortimicin A (1.1 g).

EXAMPLE 7

5-Deoxyfortimicin A tetrahydrochloride

A solution of 5-deoxytetra-N-benzyloxycarbonylfortimicin A (851 mg, 0.92 millimole) in methanolic hydrogen chloride (75 ml, 0, 2 N) is shaken within an atmosphere of hydrogen with 5% palladium on carbon (850 mg) for 4 hours. The catalyst is removed by filtration and the filtrate is evaporated to yield 5-deoxyfortimicin A tetrahydrochloride (482 mg)

The identity of the compounds of Examples 16–22 were confirmed by carbon magnetic resonance spectra. The spectra were recorded in deuterochloroform (Examples 1–5) and deuterium oxide (Examples 6–7). Only signals assigned to the carbons of the fortimicin A skeleton are shown in Table I and these are described in ppm downfield from tetramethylsilane.

TABLE I

| | CARBON MAGNETIC RESONANCE SPECTRA | | | | | | |
|---|---|---|---|---|---|---|---|
| | Example 1 | Example 2 | Example 3 | Example 4 | Example 5 | Example 6 | Example 7 |
| $C_1$ | 52.2 | 54.7 | 53.8 | 53.4 | 53.4 | 54.3 | 48.8 |
| $C_2$ | 77.3 | 30.6 | 29.6 | 68.3 | 69.1 | 69.3 | 70.9 |
| $C_3$ | 72.6 | 67.2 | 74.3 | 72.6 | 71.3 | 72.9 | 77.0 |
| $C_4$ | 57.7 | 56.1 | 57.5 | 57.3 | 57.3 | 56.9 | 55.2 |
| $C_5$ | 81.9 | 27.5 | 27.5 | 81.8 | 27.1 | 27.2 | 27.3 |
| $C_6$ | 74.2 | 73.6 | 76.2 | 72.6 | 67.5 | 67.4 | 76.1 |
| $C_1'$ | 99.4 | 96.0 | 98.4 | 98.7 | 94.7 | 95.3 | 97.7 |
| $C_2'$ | 49.9 | 50.6 | 51.0 | 50.0 | 50.2 | 50.2 | 51.1 |
| $C_3'$ | 23.9 | 24.4 | 26.7 | 24.4 | 24.7 | 24.5 | 26.3 |
| $C_4'$ | 26.4 | 27.2 | 27.1 | 27.1 | 27.1 | 27.2 | 27.3 |
| $C_5'$ | 71.2 | 71.4 | 73.5 | 71.5 | 71.3 | 71.3 | 73.1 |
| $C_6'$ | 49.9 | 49.8 | 51.0 | 50.0 | 49.4 | 49.6 | 50.0 |
| $C_7'$ | 17.5 | 18.5 | 17.7 | 18.1 | 18.2 | 18.2 | 17.3 |
| $OCH_3$ | 60.5 | 60.0 | 56.4 | 60.9 | 61.0 | 60.0 | 56.6 |
| $NCH_3$ | 31.8 | 35.4 | 32.5 | 31.4 | 32.3 | 34.8 | 29.4 |
| Glycine | 43.1 | 43.4 | 49.9 | 43.1 | 43.3 | 43.3 | 43.1 |
| Glycine | 169.9 | 168.2 | 179.7 | 169.4 | 169.7 | 168.4 | 180.0 |

Assignments have been made by analogy with like carbons in other fortimicin derivatives and from known effects of structures on CMR chemical shifts. Interchanges between assignments to Cs of resonances of similar chemical shifts does not affect characterization or structural inferences drawn.

EXAMPLE 8

In Vitro Antibiotic Activities of 5-deoxyfortimicin A tetrahydrochlorides and 2,5-dideoxyfortimicin A tetrahydrochloride The in vitro antibiotic activities are determined by a two-fold dilution test using Mueller-Hinton agar, 10 ml per Petri plate. The inoculum of approximately $1 \times 10^5$ of the indicated test organism is delivered by the Steer's replicator. The test is incubated at 37° C. for 24 hours. The minimum inhibitory concentrations (MIC), listed in Table II, are expressed in mcg/ml.

TABLE II

In Vitro Antimicrobial Activity of 2,5-Dideoxyfortimicin A tetrahydrochloride and 5-Deoxyfortimicin A tetrahydrochloride

| | Minimum Inhibitory Concentrations (mcg/ml) | |
|---|---|---|
| Organism | 2,5-dideoxy-fortimicin A . 4 HCl | 5-deoxyfortimicin A . 4 HCl |
| *Escherichia coli* R₃ | 10 | 10 |
| *Streptococcus faecalis* ATCC 10541 | 10 | 10 |
| *Pseudomonas aeruginosa* BMH #1 | 10 | 10 |
| *Staphylococcus aureus* ATCC 6538P | 0.63 | 0.63 |
| *Escherichia coli* ATCC 26 | 2.5 | 2.5 |
| *Bacillus subtilis* U. of Ill. 10707 | 2.5 | 0.63 |
| *Proteus vulgaris* ATCC 6897 | 2.5 | 5.0 |
| *Shigella sonnei* ATCC 9290 | 2.5 | 5.0 |
| *Salmonella typhi* ATCC 9992 | 2.5 | 1.3 |
| *Klebsiella pneumoniae* ATCC 10031 | 0.63 | 1.3 |

The compounds of this invention are active as systemic antibiotics when injected by parenteral routes of administration, i.e., by the intramuscular, intravenous, intraparitoneal or subcutaneous routes of administration. The compounds can also be adminstered orally in those instances where it is desirable to sterilize the intenstinal tract and can additionally be applied topically or rectally.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides, such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized, by for example, filtration through a bacteria-retaining filter, by incorporating sterilizing agents into the compositions. They can also be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 10 to 200 mg/kg of body weight daily are administered to a mammalian patient suffering from an infection caused by susceptible organism.

We claim:

1. A fortimicin antibiotic selected from the group consisting of 5-deoxyfortimicins and 2,5-dideoxyfortimicins represented by the formula:

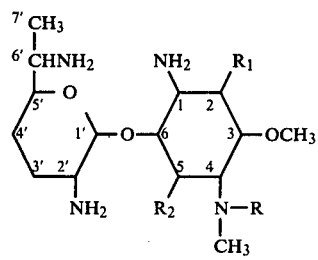

wherein R is selected from the group consisting of acyl, hydroxyacyl, aminoacyl, N-monoloweralkylaminoacyl, N,N-diloweralkylaminoacyl, hydroxyacyl, hydroxy-substituted aminoacyl or an amino acid residue other than glycyl, loweralkyl, aminoloweralkyl, hydroxyloweralkyl, N-monoloweralkylaminoloweralkyl, N-N-diloweralkylaminoloweralkyl or hydroxy-substituted aminoloweralkyl; $R_1$ is hydrogen or hydroxy; and $R_2$ is hydrogen or hydroxy with the limitation that either $R_1$ and $R_2$ each are hydrogen or when only one of $R_1$ or $R_2$ are hydrogen, $R_2$ is hydrogen and $R_1$ is hydroxy and $R_1$ and $R_2$ both cannot be hydroxy.

2. A compound of claim 1 wherein $R_2$ is hydrogen, $R_1$ is hydroxy and the compound is represented by the formula

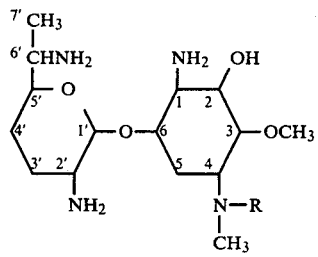

3. A compound of claim 2:5 -deoxyfortimicin A or a pharmaceutically acceptable salt thereof.

4. A compound of claim 2: 5-deoxyfortimicin A tetrahydrochloride.

5. A compound of claim 2:5-deoxyfortimicin B or a pharmaceutically acceptable salt thereof.

6. A, 2,5-dideoxyfortimicin of claim 1 wherein $R_1$ and $R_2$ each are hydrogen and R is a defined in claim 1 and the compound is represented by the formula:

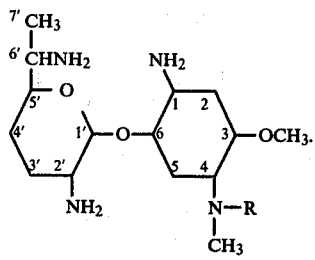

7. A compound of claim 6:2,5-dideoxyfortimicin A or a pharmaceutically acceptable salt thereof.

8. A compound of claim 6:2,5-dideoxyfortimicin A tetrahydrochloride.

9. A pharmaceutical composition comprising an antibacterially effective amount of a compound of claim 1 and a pharmaceutically acceptable carrier or diluent.

10. The composition of claim 9 wherein said compound is 5-deoxyfortimicin A or a pharmaceutically acceptable salt thereof.

11. The composition of claim 9 wherein said compound is 5-deoxtfortimicin A tetrhydrochloride.

12. The composition of claim 9 wherein said compound is 2,5 -dideoxyfortimicin A or a pharmaceutically acceptable salt thereof.

13. The composition of claim 9 wherein said compound is 2,5 -dideoxyfortamicin A tetrahydrochloride.

14. An intermediate for the preparation of 5-deoxyfortimicins represented by the formulae:

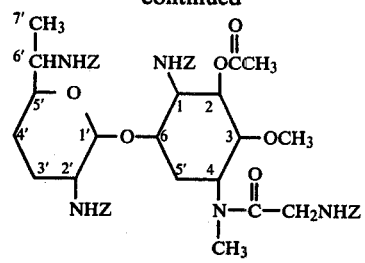

wherein Z is benzyloxycarbonyl.

15. A compound of claim 14: 2-0-acetyltetra-N-benzyloxycarbonylfortimicin A-5-0 -thiocarbonylimidazolide.

16. A compound of claim 14: 2-O-acetyl-5-deoxytetra-N-benzyloxycarbonylfortimicin A.

17. A compound of claim 14:5 -deoxytetra-N-benzyloxycarbonylfortimicin A.

18. An intermediate for the preparation of 2,5 -dideoxyfortimicins represented by the formulae:

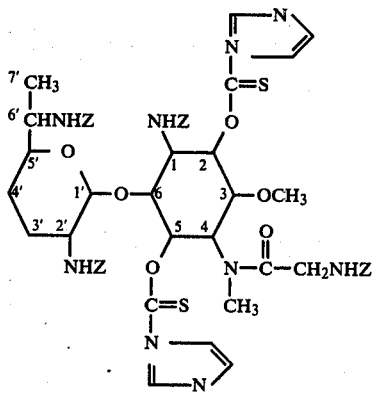

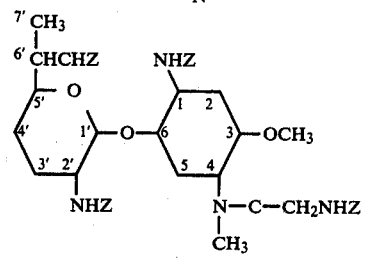

wherein Z is benzyloxycarbonyl.

19. A compound of claim 18: tetra-N-benzyloxycarbonylfortimicin A- 2,5-di-O-thiocarbonylimidazole.

20. A compound of claim 18:2,5-dideoxytetra-N-benzyloxycarbonylfortimicin A.

* * * * *